United States Patent
Shibasaki et al.

(10) Patent No.: US 6,632,955 B1
(45) Date of Patent: *Oct. 14, 2003

(54) OPTICALLY ACTIVE NITRO ALCOHOL DERIVATIVES, OPTICALLY ACTIVE AMINO ALCOHOL DERIVATIVES, AND PROCESS FOR PREPARING THE SAME

(75) Inventors: Masakatsu Shibasaki, Tokyo (JP); Hiroaki Sasai, Chiba (JP); Yasuo Urata, Kanagawa (JP); Mamoru Fujita, Kanagawa (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,135
(22) PCT Filed: Nov. 20, 1997
(86) PCT No.: PCT/JP97/04240
§ 371 (c)(1), (2), (4) Date: Sep. 1, 1999
(87) PCT Pub. No.: WO98/24753
PCT Pub. Date: Jun. 11, 1998

(30) Foreign Application Priority Data

Dec. 2, 1996 (JP) .............................. 8-336425

(51) Int. Cl.$^7$ ................................ C07F 7/04
(52) U.S. Cl. ...................................... 556/422
(58) Field of Search ................. 556/413, 422; 568/708, 704

(56) References Cited

U.S. PATENT DOCUMENTS

| | | | |
|---|---|---|---|
| 4,340,600 A | 7/1982 | Brenner et al. | |
| 4,933,505 A | 6/1990 | Barrett et al. | |
| 5,108,363 A | 4/1992 | Tuttle et al. | |
| 5,514,694 A | 5/1996 | Powers et al. | |

FOREIGN PATENT DOCUMENTS

| | | |
|---|---|---|
| DE | 1 233 410 | 2/1967 |
| DE | 2229894 | 6/1972 |
| JP | 57-16864 | 1/1982 |
| JP | 58-203950 | 11/1983 |
| JP | 2-17048 | 1/1990 |
| JP | 6-87800 | 3/1994 |
| JP | 7-242543 | 9/1995 |
| WO | 96/35685 | 11/1996 |

OTHER PUBLICATIONS

Zhao et al., "A Practical Synthesis of 4–(3',4'–Dihydroxylphenyl)–1,2,3,4–Tetrahydroisoquinoline", Org. Prep. Proced. Int. (1995), vol. 27, No. 4, pp. 513–516.

Nagren et al., "Selective Synthesis of Racemic 1–$^{11}$C–Labelled Norepinephrine, Octopamine, Norphenylephrine and Phenylethanolamine using ($^{11}$C) Nitromethane", Appl. Radiat. Isot. (1994), vol. 45, No. 4, pp. 515–521.

Kulikov et al., "Synthesis of 3–O–Methylated Derivatives of Catecholamines", Zh. Org. Khim. (1992), vol. 28, No. 2, pp. 348–358.

Kim et al., "Synthesis of Tunichromes Mm–1 and Mm–2, Blood Pigments of the Iron–Assimilating Tunicate, Molgula Manhattensis", Tetrahedron Lett. (1990), vol. 31, No. 49, pp. 7119–7122.

Chem. Abstr., vol. 105, No. 19, Nov. 10, 1986 (Columbus, OH, USA), p. 715, column 2, the abstract No. 172151c, Yang, P.W. et al. 'Improved synthesis of adrenaline', Hua Hsueh, 1985, 43(1), 19–29 (Ch).

Nakamura et al., "Postharvest Berry Drop of Seedless Berries Produced by GA Treatment in Grape Cultivar 'Kyoho'", Tohoku J. Agric. Res. (1985), vol. 35, Nos. 2–4, pp. 81–89.

Leclerc et al., "Synthesis and Structure–Activity Relationships among α–Adrenergic Receptor Agonists of the Phenylethanolamine Type", J. Med. Chem. (1980), vol. 23, No. 7, pp. 738–744.

Chem. Abstr., vol. 88, No. 3, Jan. 16, 1978, (Columbus, OH, USA), p. 583, column 2, the abstract No. 22320y, Siatra T et al., 'Derivatives of 1–(3', 4'–dimethoxyphenyl)–2–aminoacetylaminoethanol', Chem. Chron. 1977, 6(3), 471–477 (Eng).

(List continued on next page.)

Primary Examiner—Samuel Barts
(74) Attorney, Agent, or Firm—Wenderoth, Lind & Ponack, L.L.P.

(57) ABSTRACT

Optically active 1-substituted phenyl-2-nitro alcohol derivatives having the formula (1)

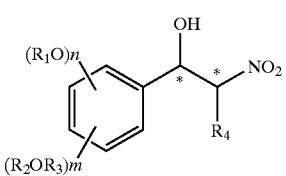

(Formula 1)

and the process for producing thereof, and 1-substituted phenyl-2-amino alcohol derivatives having the formula (2)

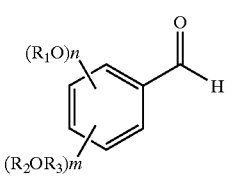

(Formula 2)

and the process for producing thereof from the optically active 1-substituted phenyl-2-nitro alcohol derivatives. From these nitro alcohols, pharmaceuticals such as (R)-albutamin and (R)-sarmeterol useful as a bronchodilator is obtained via optically active amino alcohols which are useful pharmaceutical intermediates.

1 Claim, No Drawings

OTHER PUBLICATIONS

Crowell et al., "A Kinetic Analysis of Nitrostyrene Hydrolysis and the Knoevenagel Condensation", J. Amer. Chem. Soc. (1973), vol. 95, No. 20, pp. 6781–6786.

Chem. Abstr., vol. 67, No. 7, Aug. 14, 1967 (Columbus, OH, USA), p. 3058, column 1–2, the abstract number No. 32454a, Karl Wismayr et al., 'Phenylnitroethanols', Ger, 1233410(CI.CO7C), Feb. 2, 1967, Appl. Jun. 15, 1961.

Seebach et al., "Diastereoselective Synthesis of Nitroaldol Derivatives", Helvetica Chimica Acta, vol. 65, No. 4 (1982), pp. 1101–1133.

Eyer et al., "1–2–Nitro–1, 3–alkanediols by Stereoselective Addition of Nitroethanol to Aldehydes. On the Asymmetric Electrophilic Addition to Double Bonds", J. Am. Chem. Soc., vol. 107 (1985), pp. 3601–3606.

Sasai et al., "Effects of Rare Earth Metals on the Catalytic Asymmetric Nitroaldol Reaction", Tetrahedron Letters, vol. 34, No. 16 (1993), pp. 2657–2660.

XP002127516 (Database Crossfire [Online] Beilstein Informationssysteme GmbH Frankfurt DE) & Bull. Soc. Chim. Fr. (1949), p. 536.

XP002127517 (Database Crossfire [Online] Beilstein Informationssysteme GmbH Frankfurt DE) & Can. J. Chem., vol. 39 (1961), pp. 1143–1147.

XP002127518 (Database Crossfire [Online] Beilstein Informationssysteme GmbH Frankfurt DE) & J. Org. Chem., vol. 16 (1951), p. 1573.

XP002127519 (Database Crossfire [Online] Beilstein Informationssysteme GmbH Frankfurt DE) & Chem. Ber., vol. 46 (1913), p. 1039.

XP002127520 (Database WPI Section CH., week 199749; Class B05, AN 1997–532738) & JP 09255631 A (1997).

OPTICALLY ACTIVE NITRO ALCOHOL DERIVATIVES, OPTICALLY ACTIVE AMINO ALCOHOL DERIVATIVES, AND PROCESS FOR PREPARING THE SAME

TECHNICAL FIELD

The present invention relates to optically active 1-substituted phenyl-2-nitro alcohol derivatives and the process for producing thereof, to optically active 1-substituted phenyl-2-amino alcohol derivatives and the process for producing thereof, and to the process for producing (R)-albutamin and (R)-sarmeterol using these compounds.

The optically active nitro alcohols of the present invention are useful in the medical field, particularly as a synthetic intermediate of nitrogenous compounds useful for thrombotic diseases, for example, cerebral infarction, myocardial infarction, angina pectoris, and peripheral arterial occlusion; of optically active albuterol, optically active sarmeterol, (R)-albutamin, and optically active terbutaline hydrochloride which are useful as a bronchodilator; and of optically active bamethan sulfate useful as a vasodilator. And these compounds can be produced in high yields and industrially advantageously with the process for producing thereof of the present invention.

The optically active amino alcohols of the present invention can be obtained from the above optically active nitro alcohols, and they are also useful intermediates of pharmaceuticals such as a thrombolytic agent, a central nervous system agent, an antiadipogenous agent and an antiasthmatic agent.

BACKGROUND ART

The optically active nitro alcohols of the present invention are novel substances obtained by the nitro-aldol reaction between nitromethane and benzaldehyde derivatives.

It is widely known that such a nitro-aldol reaction proceeds in theipresence of a base. For example, in Japanese Patent Application Laid-Open No. 58-203950, there is disclosed the nitro-aldol reaction performed in the presence of triethylamine which gives a racemic modification of ben-znitro alcohol. And in Tetrahedron Letters (1975) p.4057, there is disclosed the reaction between 2-chlorobenzaldehyde and nitroethane under a catalyst of an optically active compound which gives an asymmetric nitro alcohol in which a substituent is a chloride.

Further, the present inventors has reported in Tetrahedron Letters (1993) Vol. 34, p. 2657 that the reaction between benzaldehyde and nitromethane under a catalyst of lanthanum-lithium-(R)-binaphthol complex at −50° C. gives (S)-1-phenyl-2 nitro ethanol in a yield of 84% (40% e.e.), and when carried out under a catalyst of samarium-lithium-(R)-binaphthol complex at −40° C., the reaction gives the same compound in a yield of 90% (62% e.e.) ((R) or (S) in the name of leach compound represents R or S isomer, respectively, showing the compound's configuration).

The yields and optical purities described above, however, are not satisfactory ones. In addition, an asymmetric nitro-aldol reaction of benzaldehyde compounds having a hydroxyl group or those having a hydroxyl group with a protecting group has not been found yet and the reaction products, optic ally active 1-substituted phenyl-2-nitro alcohol derivatives, have not been known yet, either.

But at the same time, it is hoped now that pharmaceuticals produced from benznitro alcohol derivatives will be supplied in the form of a single optical isomer rather than in the form of a racemic modification. The reason is that, when only one type of structure is therapeutically effective, the other type of optically active substance is no better than impurities and likely to cause adverse effects. In order to meet such a demand, various types of asymmetric synthesis and optical resolution of a racemic modification have been carried out as a method of obtaining pharmaceuticals of optically active substances.

However, as described above, the nitro-group containing compounds (intermediates) of the present invention have not been known yet, and the only example is (S)-1-phenyl-2-nitroethanol, which has no substituent, reported by the present inventors. Accordingly, the process for producing a group of pharmaceuticals which are to be produced from optically active 1-substituted phenyl-2-nitro alcohol derivatives has not been known, either.

The optically active 1-substituted phenyl-2-amino alcohol derivatives of the present invention are a group of the compounds obtained from the novel optically active 1-substituted phenyl-2-nitro alcohol derivatives of the present invention.

On the other hand, as a method of producing optically active 1-substitute phenyl-2-amino alcohol derivatives, various types of asymmetric synthesis and optical resolution of a racemic modification have been carried out, and various processes for producing compounds similar to these ones have been also reported.

For example, as a method using optical resolution, in Japanese Patent Application Laid-Open No. 64-9979 (Japanese Patent Publication No. 4-48791), there is disclosed a method of producing (R) isomer of 2-amino-1-(3-chlorophenyl) ethanol from the racemic modification using N-(t-butoxycarbonyl)-D-alanine. And in Japanese Patent Application Laid-Open No. 2-85247, there is disclosed the method of subjecting the racemic modification of 2-amino-1-(4-chlorophenryl) ethanol to optical resolution using D-tartaric acid.

As a method using an asymmetric reduction reaction, for example, in Chemical and Pharmaceutical Bulletin (1995) vol. 43–5, p.738, there is disclosed the process for producing (S)-1-phenyl-2-[N-(2-chloroethyl)] aminoethanol hydrochloride from 2-[N-(2-chloroethyl)] aminophenone hydrochloride.

And as a method using microorganisms, for example, in Chemistry Express (1989) vol. 4–9, p.621, there is disclosed the process for producing optically active 2-amino-1-phenylethanol from 2-amino-1-phenylethanol and α-aminoacetophenone as raw materials by microorganisms of Staphyrococcus, Micrococcus, Rhodococcus, and Niseria.

Further, in Japanese Patent Application Laid-Open No. 8-98697, there is disclosed the process for producing optically active 2-amino-1-phenylethanol derivatives from 2-amino-1-phenylethanol derivatives using various microorganisms.

With the method using optical resolution, however, even if optical resolution is carried out perfectly, the maximum yield expected is only 50% per reaction, and moreover, it is difficult to collect the optically active substances desired in a good yield. Accordingly, in order to improve the yield of optically active substances, it becomes necessary to further racemize unnecessary chiral compounds and to carry out optical resolution of the obtained racemic modifications repeatedly. Thus, using optical resolution can not produce the optically active substances desired effectively and industrially, therefore it can not be a satisfactory method.

Further, with the method using a usual hydrogen-reduction reaction of which typical example is the above asymmetric reduction reaction, unless the hydrogen pressure is high, the reaction often does not proceed. Thus the method is not appropriate, and moreover, since it has to use a special catalyst, the treatment of the catalyst has been a problem.

For the reduction reaction of optically active nitro alcohols, U.S. Pat. No. 5,099,067 reports that the reduction reaction of erythro/threo forms of β-nitro alcohol proceeds at room temperature by adding ammonium formate.

For example, in Japanese Patent Application Laid-Open No. 6-256270, the present inventors report that (S)-(−)-propranolol is obtained in a yield of 90% from (S)-3-(α-naphthoxy)nitropropane-2-ol in the presence of $PtO_2$ at 50° C. under atmospheric pressure. Further, the present inventors report in Journal of the Organic Chemistry (1995) vol. 60, p. 7388 that 2-amino-1,3-alkyldiol is obtained in a yield of 71% in the presence of Pd—C.

These reduction reactions, however, are limited to the cases where the reduction reaction occurs on racemic modifications, and where, when the reaction occurs on optically active substances, a phenyl group has no substituent or only chlors as a substituent. There is no prior art known which is related directly to the reduction reaction intended by the present invention during which a steric structure of phenyl group having a hydroxyl group is maintained.

A racemic modification of 1-phenyl-2-aminoethanol is a known compound, for example, in Japanese Patent Application Laid-Open No. 58-203950, there is disclosed the synthetic method in which 1-(3,4-dihidroxyphenyl)-2-nitroethanol is subjected to a catalytic hydrogen addition reaction using Raney nickel to proceed the reduction reaction quantitatively, so as to obtain a racemic modification of 1-(3,4-dihidroxyphenyl)-2-aminoethanol; however, the disclosure makes no concrete reference to the optically active substances of 1-substituted phenyl-2-aminoethanol.

Thus, optically active 1-substituted phenyl-2-nitroethanol derivatives have not existed to date, and the products obtained by the reduction of the nitro group thereof, optically active 1-substituted phenyl-2-aminoethanol derivatives, have not been produced.

On the other hand, 1-substituted phenyl-2-aminoethanol derivatives are widely known compounds as a useful pharmaceutical intermediate.

For example, European Patent No. 0,006,735 specification describes that the intended pharmaceuticals can be synthesized by reacting a racemic and optically active amino alcohol compound with a carbonyl compound or a halide; however, actually disclosed in its embodiments is only the process for producing racemic sarmeterol by reacting a racemic amino alcohol compound with a carbonyl compound or a halide.

In U.S. Pat. No. 5,442,118 specification there is disclosed the process for producing (R)-albuterol and in European Patent Publication No. 0,422,889 specification there is disclosed the process for producing (R)-sarmeterol; however, their production process is long, and the intended compound is obtained from the optically active styrene oxane derivatives which have been obtained from acetophenone derivatives as a raw material. In these patents, there is no embodiment in which the optically active 1-substituted phenyl-2-nitroethanol derivatives of the present invention are used.

Thus, optically active 1-substituted phenyl-2-nitroethanol compounds have not existed to date, therefore, the process for producing optically active albutamin and optically active sarmeterol using optically active catechol amines obtained by the reduction of the nitro group thereof has not been known.

DISCLOSURE OF THE INVENTION

The present invention has been made in light of the foregoing problems of the prior arts. Accordingly, it is an object of the present invention to provide optically active 1-substituted phenyl-2-nitro alcohol derivatives and optically active 1-substituted phenyl-2-amino alcohol derivatives obtained by reducing the optically active 1-substituted phenyl-2-nitro alcohol derivatives of the present invention both of which are useful as an intermediate of pharmaceuticals such as (R)-albutamin, (R)-sarmeterol, (R)-albuterol and (R)-terbutaline hydrochloride which are useful as a bronchodilator, and bamethan sulfate which is useful as a vasohypotonic. Another object of the present invention is to provide a process for producing these compounds. And another object of the present invention is to provide (R)-albutamin and (R)-sarmeterol produced using these compounds.

After concentrating their energy on the study to achieve the above objects, the present inventors came to know that, for the optically active nitro alcohol derivatives, a group of the intended compounds can be obtained using the group of rare earth metal complexes described by themselves in U.S. Pat. No. 5,336,653 specification and Tetrahedron Letters (1993) vol. 341 p. 2657 etc. At the same time, the present inventors came to know that, for the optically active amino alcohol derivatives, a group of the intended compounds can be easily obtained by subjecting the optically active nitro alcohol derivatives obtained as above to catalytic hydrogen addition in an organic solvent. And the present inventors found that they can achieve the above objects with these knowledge and have finally completed the present invention.

Specifically, the optically active 1-substituted phenyl-2-nitro alcohol derivatives of the present invention are characterized by the following formula (1),

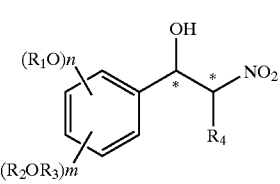

(Formula 1)

in which n and ml represent the positive integers satisfying 0<n+m≦5; $R_1$ and $R_2$ represent a hydrogen atom or a hydroxyl-protective group, respectively, and when n+m is 2 or more, $R_1$ and $R_2$ can either be independent of each other or form a ring among $R_1$s, $R_2$s, or $R_1$s plus $R_2$s; $R_3$ represents —$(CH_2)_1$—, in which 1 is 1, 2 or 3; $R_4$ represents a hydrogen atom, an alkyl group, or a hydroxymethyl group.

Suitable examples of the optically active 1-(3,4-dihydroxyphenyl)-2-nitro alcohols of the present invention are characterized by the following formula (1-1),

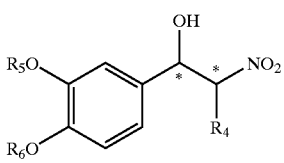

(Formula 1-1)

in which $R_5$ and $R_6$ represent a hydrogen atom or a hydroxyl-protective group, respectively, and they can either be independent of each other or form a ring; $R_4$ represents a hydrogen atom, an alkyl group, or a hydroxymethyl group.

(R)-albutamin etc., useful as a pharmaceutical, can be produced from the compounds of the above group of which $R_4$ is a hydrogen atom and isomer type is R-type, by converting the nitro group into an amino group, reacting the amino group with a carbonyl compound or an alkyl halide compound, and then eliminating the hydroxyl-protective group.

Suitable examples of the optically active 1-(3-hydroxymethyl-4-hydroxyphenyl)-2-nitro alcohols of the present invention are characterized by the following formula (1-2),

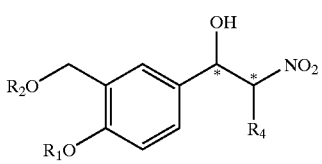

(Formula 1-2)

in which $R_1$ and $R_2$ represent a hydrogen atom or a hydroxyl-protective group, respectively, and they can either be independent of each other or form a ring; $R_4$ represents a hydrogen atom, an alkyl group, or a hydroxymethyl group.

(R)-sarmeterol, (R)-albuterol etc., useful as a pharmaceutical, can be produced from the compounds of the above group of which $R_4$ is a hydrogen atom and isomer type is R-type, by converting the nitro group into an amino group, reacting the amino group with a carbonyl compound or an alkyl halide compound, and then eliminating the hydroxyl-protective group.

Suitable examples of the optically active 1-(3,5-dihydroxyphenyl)-2-nitro alcohols of the present invention are characterized by the following formula (1-3),

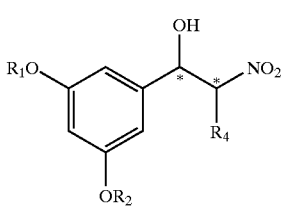

(Formula 1-3)

in which $R_1$ and $R_2$ represent a hydrogen atom or a hydroxyl-protective group, respectively, and they can either be independent of each other or form a ring; $R_4$ represents a hydrogen atom, an alkyl group, or a hydroxymethyl group.

Optically active terbutaline etc., useful as a bronchodilator, can be produced from the compounds of the above group of $R_4$ is a hydrogen atom, by converting the nitro group into an amino group, reacting the amino group with a carbonyl compound or an alkyl halide compound, and then eliminating the hydroxyl-protective group.

Suitable examples of the optically active 1-(4-hydroxyphenyl)-2-nitro alcohols of the present invention are characterized by the following formula (1-4),

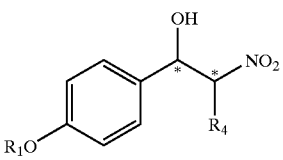

(Formula 1-4)

in which $R_1$ represents a hydrogen atom or a hydroxyl-protective group, respectively, and it can either be independent of each other or form a ring; $R_4$ represents a hydrogen atom, an alkyl group, or a hydroxymethyl group.

Optically active bamethan etc., useful as a vasohypotonic, can be produced from the compounds of the above group of which $R_4$ is a hydrogen atom, by converting the nitro group into an amino group, reacting the amino group of the amino alcohol with a carbonyl compound or an alkyl halide compound, and then eliminating the hydroxyl-protective group.

Other suitable examples of the optically active nitro alcohols of the present invention are as follows.

The optically active 1-(3,4-dihydroxyphenyl)-2-nitro alcohol derivatives (optically active 1-(3,4-di(t-butyldimethylsilolxy)phenyl)-2-nitroethanol) of formula (1-1), in which $R_4$ is a hydrogen atom, and each of $R_5$ and $R_6$ is a t-butyldimethylsiloxy group.

Optically active albutamin etc. useful as a pharmaceutical can be produced from this compound by converting the nitro group into an amino group, reacting the optically active amino alcohol with a carbonyl compound (for example, 4-(4-methoxymethoxyphenyl)butanoic acid, etc.), and then eliminating the hydroxyl-protective group.

The optically active 1-(3,4-dihydroxyphenyl)-2-nitro alcohol derivatives (optically active 1-(3,4-dimethoxyphenyl)-2-nitroethanol) of formula (1-1), in which $R_4$ is a hydrogen atom, and each of $R_5$ and $R_6$ is a methyl group.

Optically active albutamin etc. useful as a pharmaceutical can be produced from this compound by converting the nitro group into an amino group, reacting the amino alcohol with a carbonyl compound (for example, 4-(4-methoxymethoxyphenyl)butanoic acid, etc.), and then eliminating the hydroxyl-protective group.

The optically active 1-(3,4-dihydroxyphenyl)-2-nitro alcohol derivatives (optically active 1-(3,4-dibenzyloxyphenyl)-2-nitroethanol) of formula (1-1), in which $R_4$ is a hydrogen atom, and each of $R_5$ and $R_6$ is a benzyl group.

Optically active albutamin etc. useful as a pharmaceutical can be produced from this compound by converting the nitro group into an amino group, reacting the optically active amino alcohol with a carbonyl compound (for example, 4-(4-methoxymethoxyphenyl)butanoic acid, etc.), and then eliminating the hydroxyl-protective group.

The optically active 1-(3,4-dihydroxyphenyl)-2-nitro alcohol derivatives (optically active 1-(3,4-diacetoxyphenyl)-2-nitroethanol) of formula (1-1), in which $R_4$ is a hydrogen atom, and each of $R_5$ and $R_6$ is an acetyl group.

Optically active albutamin etc. useful as a pharmaceutical can be produced from this compound by converting the nitro group into an amino group, reacting the optically active amino alcohol with a carbonyl compound (for example, 4-(4-methoxymethoxyphenyl)butanoic acid, etc.), and then eliminating the hydroxyl-protective group.

The optically active 1-(3,4-dihydroxyphenyl)-2-nitro alcohol derivatives (optically active α-nitromethyl-piperonyl alcohol) of formula (1-1), in which $R_4$ is a hydrogen atom, and $R_5$ and $R_6$ are cyclized with a methylene group.

Optically active albutamin etc. useful as a pharmaceutical can be produced from this compound by converting into an amino group, reacting the optically active amino alcohol with a carbonyl compound (for example, 4-(4-methoxymethoxyphenyl)butanoic acid, etc.), and then eliminating the hydroxyl-protective group.

The optically active 2,2-dimethyl-α-nitromethyl-1,3-benzodioxan-6-methanol of formula (1-2), in which $R_4$ is a hydrogen atom, and $R_1$ and $R_2$ are cyclized.

Optically active sarmeterol etc. useful as a pharmaceutical can be produced from this compound by converting into an amino group, reacting the amino group with a carbonyl compound, and then eliminating the hydroxyl-protective group.

The optically active 1-(3,5-dibenzyloxyphenyl)-2-nitroethanol of formula (1-3), in which $R_4$ is a hydrogen atom, and each of $R_1$ and $R_2$ is a benzyl group.

Optically active terbutaline etc. useful as a pharmaceutical can be produced from this compound by converting into an amino group, reacting the amino group with a carbonyl compound, and then eliminating the hydroxyl-protective group.

The optically active 1-(4-benzoyloxyphenyl)-2-nitroethanol of formula (1-4) set forth in claim 1, characterized in that $R_4$ is a hydrogen atom and $R_1$ is a benzoyl group. Optically active bamethan etc. useful as a pharmaceutical can be produced from this compound by converting into an amino group, reacting the amino group with a carbonyl compound, and then eliminating the hydroxyl-protective group.

The process for stereoselectively producing optically active nitro alcohols of the present invention is characterized in that, when producing optically active 1-substituted phenyl-2-nitro alcohol derivatives, an aldehyde of the following formula (2),

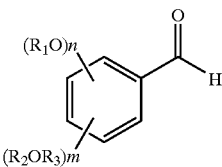

(Formula 2)

in which $R_5$ and $R_6$ represent a hydrogen atom or a hydroxyl-protective group, respectively, and they can either be independent of each other or form a ring together; $R_4$ represents a hydrogen atom, an alkyl group, or a hydroxymethyl group,
is reacted with a nitro alkane derivative of the following formula (3),

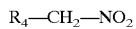

$R_4$—$CH_2$—$NO_2$ (3)

in which $R_4$ represents a hydrogen atom, an alkyl group, or a hydroxymethyl group,
in the presence of a rare earth metal complex having an optically active ligand.

Likewise, the process for stereoselectively producing optically active nitro alcohols of the present invention is characterized in that, when producing optically active 1-(3, 4-dihydroxyphenyl)-2-nitro alcohol derivatives, an aldehyde of the following formula (2-1),

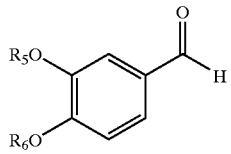

(Formula 2-1)

in which $R_5$ and $R_6$ represent a hydrogen atom or a hydroxyl-protective group, respectively, and they can either be independent of each other or form a ring together; $R_4$ represents a hydrogen atom, an alkyl group, or a hydroxymethyl group, is reacted with a nitro alkane derivative of the following formula (3),

$R_4$—$CH_2$—$NO_2$ (3)

in which $R_4$ represents a hydrogen atom, an alkyl group, or a hydroxymethyl group, in the presence of a rare earth metal complex having an optically active ligand.

Likewise, the process for stereoselectively producing optically active nitro alcohols of the present invention is characterized in that, when producing optically active 1-(3-hydroxymethyl-4-hydroxyphenyl)-2-nitro alcohol derivatives, an aldehyde of the following formula (2-2),

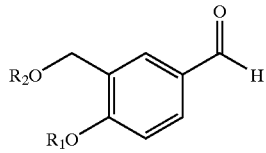

(Formula 2-2)

in which $R_1$ and $R_2$ represent a hydrogen atom or a hydroxyl-protective group, respectively, and they can either be independent of each other or form a ring together; $R_4$ represents a hydrogen atom, an alkyl group, or a hydroxymethyl group, is reacted with a nitro alkane derivative of the following formula (3),

$R_4$—$CH_2$—$NO_2$ (3)

in which $R_4$ represents a hydrogen atom, an alkyl group, or a hydroxymethyl group, in the presence of a rare earth metal complex having an optically active ligand.

Likewise, the process for stereoselectively producing optically active nitro alcohols of the present invention is characterized in that, when producing optically active 1-(3, 5-dihydroxyphenyl)-2-nitro alcohol derivatives, an aldehyde of the following formula (2-3), (Formula 2-3)

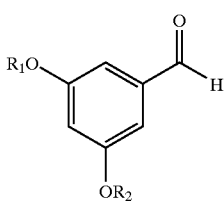

in which $R_1$ and $R_2$ represent a hydrogen atom or a hydroxyl-protective group, respectively, and they can either be independent of each other or form a ring together; $R_4$ represents a hydrogen atom, an alkyl group, or a hydroxymethyl group, is reacted with a nitro alkane derivative of the following formula (3),

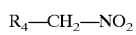 (3)

in which $R_4$ represents a hydrogen atom, an alkyl group, or a hydroxymethyl group, in the presence of a rare earth metal complex having an optically active ligand.

Likewise, the process for stereoselectively producing optically active nitro alcohols of the present invention is characterized in that, when producing optically active 1-(4-hydroxyphenyl)-2-nitro alcohol derivatives, an aldehyde of the following formula (2-4), (Formula 2-4)

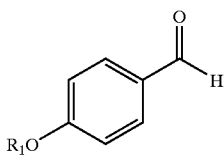

in which $R_1$ represents a hydrogen atom or a hydroxyl-protective group; $R_4$ represents a hydrogen atom, an alkyl group, or a hydroxymethyl group, is reacted with a nitro alkane derivative of the following formula (3),

 (3)

in which $R_4$ represents a hydrogen atom, an alkyl group, or a hydroxymethyl group, in the presence of a rare earth metal complex having an optically active ligand.

Suitable examples of the process for stereoselectively producing optically active nitro alcohols of the present invention include the following embodiments.

The process for stereoselectively producing optically active nitro alcohol derivatives characterized in that, when producing an optically active 1-(3,4-dihydroxyphenyl)-2-nitro alcohol derivative of the formula (1-1) in which $R_4$ is a hydrogen atom and each of $R_5$ and $R_6$ is a t-butyldimethylsiloxy group (optically active 1-(3,4-di(t-butyldimethylsiloxy)phenyl)-2-nitroethanol), an aldehyde of the following formula (4)

(Formula 4)

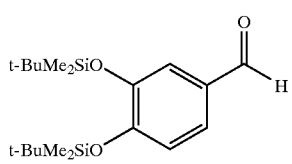

is reacted with nitromethane in the presence of a rare earth metal complex having an optically active ligand.

The process for stereoselectively producing optically active nitro alcohol derivatives characterized in that, when producing an optically active 1-(3,4-dihydroxyphenyl)-2-nitro alcohol derivative of the formula (1-1) in which $R_4$ is a hydrogen atom and each of $R_5$ and $R_6$ is a methyl group (optically active 1-(3,4-dimethoxyphenyl)-2-nitroethanol), an aldehyde of the following formula (5)

(Formula 5)

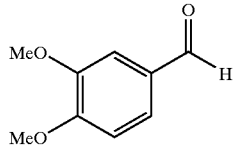

is reacted with nitromethane in the presence of a rare earth metal complex having an optically active ligand.

The process for stereoselectively producing optically active nitro alcohol derivatives characterized in that, when producing an optically active 1-(3,4-dihydroxyphenyl)-2-nitro alcohol derivative of the formula (1-1) in which $R_4$ is a hydrogen atom and each of $R_5$ and $R_6$ is a benzyl group (optically active 1-(3,4-dibenzyloxyphenyl)-2-nitroethanol), an aldehyde of the following formula (6)

(Formula 6)

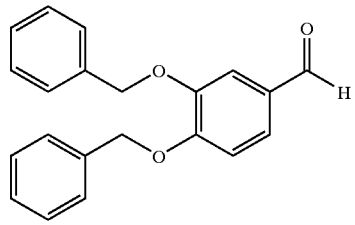

is reacted with nitromethane in the presence of a rare earth metal complex having an optically active ligand.

The process for stereoselectively producing optically active nitro alcohol derivatives characterized in that, when producing an optically active 1-(3,4-dihydroxyphenyl)-2-nitro alcohol derivative of the formula (1-1) in which $R_4$ is a hydrogen atom and each of $R_5$ and $R_6$ is a acetyl group (optically active 1-(3,4-diacetoxyphenyl)-2-nitroethanol), an aldehyde of the following formula (7)

(Formula 7)

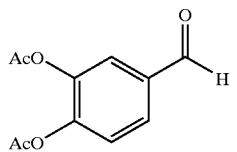

is reacted with nitromethane in the presence of a rare earth metal complex having an optically active ligand.

The process for stereoselectively producing optically active nitro alcohol derivatives characterized in that, when producing an optically active 1-(3,4-dihydroxyphenyl)-2-nitro alcohol derivative of the formula (1-1) in which $R_4$ is a hydrogen atom and $R_5$ and $R_6$ are cyclized with a methylene group (optically active α-nitromethyl-piperonyl alcohol), an aldehyde of the following formula (8)

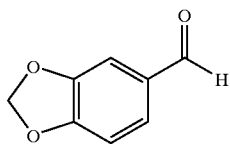

(Formula 8)

is reacted with nitromethane in the presence of a rare earth metal complex having an optically active ligand.

The process for stereoselectively producing optically active nitro alcohol derivatives characterized in that, when producing an optically active 2,2-dimethyl-α-nitromethyl-1,3-benzodioxane-6-methanol of the formula (1-2) in which $R_4$ is a hydrogen atom and $R_1$ and $R_2$ are cyclized, an aldehyde of the following formula (9)

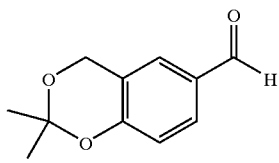

(Formula 9)

is reacted with nitromethane in the presence of a rare earth metal complex having an optically active ligand.

The process for stereoselectively producing optically active nitro alcohol derivatives characterized in that, when producing an optically active 1-(3,5-dibenzyloxyphenyl)-2-nitroethanol of the formula (1-3) in which $R_4$ is a hydrogen atom and each of $R_1$ and $R_2$ is a benzyl group, an aldehyde of the following formula (10)

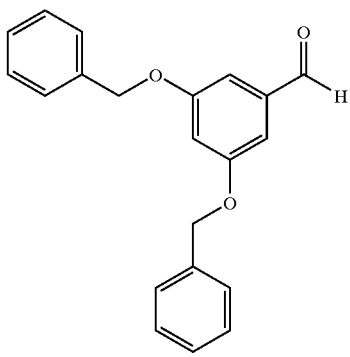

(Formula 10)

is reacted with nitromethane in the presence of a rare earth metal complex having an optically active ligand.

The process for stereoselectively producing optically active nitro alcohol derivatives characterized in that, when producing optically active 1-(4-benzoyloxyphenyl)-2-nitroethanol of the formula (1-4) as described in claim 1 in which $R_4$ is a hydrogen atom and $R_1$ is a benzoyl group, an aldehyde of the following formula (11)

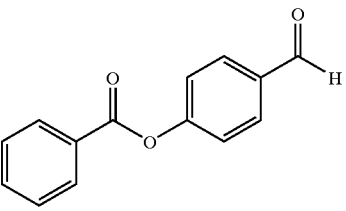

(Formula 11)

is reacted with nitromethane in the presence of a rare earth metal complex having an optically active ligand.

In the process for stereoselectively producing optically active nitro alcohol derivatives as described above, the rare earth metal complexes as above are preferably prepared from an alkoxide of Y, La, Nd, Sm, Eu, Gd, Tb, Dy, Pr or Yb, or a trichloride of these rare earth metals; an optically active 1,1'-bi-2-naphthol derivative of the following formula (12)

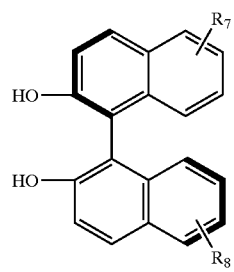

(Formula 12)

or the following formula (13)

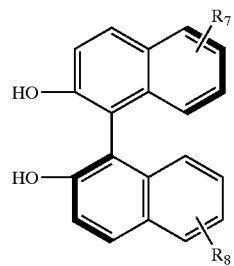

(Formula 13)

in which each of $R_7$ and $R_8$ independently represent a hydrogen atom, an alkyl group of $C_1$–$C_4$, an ethynyl group, a trialkylsilylethynyl group, or a phenyl group, and $R_7$ can be at any position of 4, 5, 6 and 7, and $R_8$ at any position of 4', 5', 6' and 7';

and an alkaline metal compound of lithium, sodium, or potassium.

Further, in the process for stereoselectively producing optically active nitro alcohol derivatives as described above, it is more preferable that the rare earth metal complexes to be used are prepared in such a way that the composition ratio of the alkoxide or trichloride of the above rare earth metals, the optically active 1,1'-bi-2-naphthol compound, and the alkaline metal is within the range of 1:1–3:0–10.

The optically active 1-substituted phenyl-2-amino alcohol derivatives of the present invention are characterized by the following formula (14),

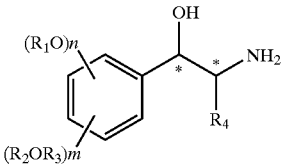

(Formula 14)

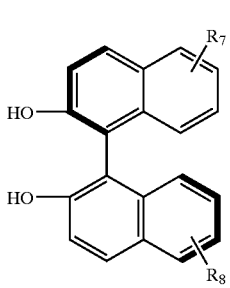

(Formula 12)

in which n and m represent the positive integers satisfying $0<n+m\leq5$; $R_1$ and $R_2$ represent a hydrogen atom or a hydroxyl-protective group, respectively, and when n+m is 2 or more, $R_1$ and $R_2$ can either be independent of each other or form a ring among $R_1$s, among $R_2$s, and among $R_1$(s) and $R_2$(s); $R_3$ represents —$(CH_2)_l$— in which l represents 0, 1, or 3; $R_4$ represents a hydrogen atom, an alkyl group, or a hydroxymethyl group.

Suitable examples of the optically active 1-substituted phenyl-2-amino alcohol derivatives of the present invention are the optically active 1-(3,4-dihydroxyphenyl)-2-amino alcohol derivatives of the following formula (14-1)

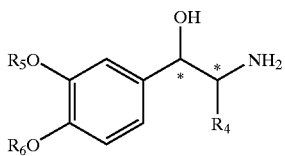

(Formula 14-1)

in which $R_5$ and $R_6$ represent a hydrogen atom or a hydroxyl-protective group, respectively, and they can either be independent of each other or form a ring; $R_4$ represents a hydrogen atom, an alkyl group, or a hydroxymethyl group.

And the process for producing the optically active amino alcohol derivatives of the present invention is characterized in that, when producing optically active 1-substituted phenyl-2-amino alcohol derivatives, the optically active 1-substituted phenyl-2-nitro alcohol derivatives described above are stereoselectively reduced.

Pharmaceuticals such as optically active albutamin and sarmeterol can be produced by reacting these optically active amino alcohol derivatives with a carbonyl compound or an alkyl halide so as to introduce an alkyl group etc. into the amino group, and then eliminating hydroxyl-protective group; therefore, the optically active nitro alcohol derivatives and optically active amino alcohols of the present invention are useful pharmaceutical intermediates.

Now the process for producing the optically active nitro alcohol derivatives of the present invention will be described below.

In general, nitro-aldol reaction between a benzaldehyde derivative and a nitro alkane proceeds in the presence of a basic catalyst. The asymmetric nitro-aldol reaction according to the present invention can be carried out by the reaction of a benzaldehyde derivative and a nitro alkane in the presence of a rare earth metal complex having an optically active ligand.

In this case, as a supplying source of an optically active ligand, preferable are optically active 1,1'-bi-2-napthol derivatives of the following formula (12)

or the following formula (13)

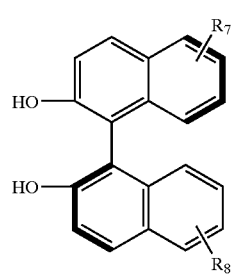

(Formula 13)

in which $R_7$ and $R_8$ independently represent a hydrogen atom, an alkyl group of $C_1$–$C_4$, an ethynyl group, a trialkyl-silylethynyl group, or a phenyl group, and $R_7$ can be at any position of 4, 5, 6 and 7, and $R_8$ at any position of 4', 5', 6' and 7'.

The process for preparing a rare earth metal complex solution can be briefly illustrated by the following (reaction equation 1), Reaction equation 1

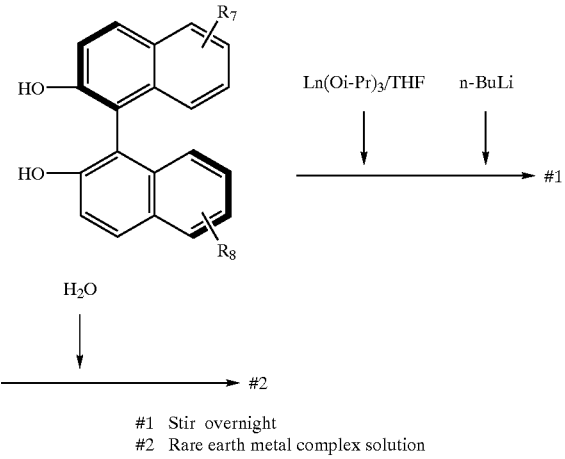

1 Stir overnight
2 Rare earth metal complex solution although the process is described in detail in the foregoing literature. This is exemplary of the process of this invention, and it is to be understood that the invention is not intended to be limited to the specific process.

The present invention uses only one type of isomer, R-type or S-type, of the above optically active binaphthols. For the optically active binaphthols, $R_7$ can be at any position of 3, 4, 5, 6 and 7, and $R_8$ at any position of 3', 4', 5', 6' and 7', and it is found at present that, in terms of yield and optical purity, good results are obtained particularly from the optically active binaphthol having substituents at 6 and 6' positions.

Examples of $R_7$ and $R_8$ include a hydrogen atom; an alkyl group of methyl, ethyl, propyl, isopropyl, n-butyl, s-butyl, or t-butyl; a phenyl group; an alkenyl group; a trialkylsilylethynyl group (in this case, alkyl includes methyl, ethyl, propyl, isopropyl, n-butyl, s-butyl, or t-butyl, tow alkyls can be different from each other or can be the same); a cyano group; and a halogen; and any combination can be adopted.

Examples of the rare earth metals of the rare earth metal compounds include Y, La, Nd, Sm, Eu, Gd, Tb, Dy, Pr, and Yb, any of the metals can be used suitably.

Examples of the rare earth metal compounds include an alkoxide (including methoxide, ethoxide, propoxide, isopropoxide, n-butoxide, s-butoxide, and t-butoxide), a chloride (including both an anhydride and a hydride), and a nitrate, and any of them can be used preferably.

Examples of the alkaline metal compounds used for the preparation of rare earth metal complexes include alkylalkaline metals (for example, methyllithium and n-butyllithium), alkaline metal hydroxides (for example, lithium hydroxide, sodium hydroxide and potassium hydroxide).

Examples of solvents used in the preparation of a rare earth metal complex solution include THF; however, the present invention is not limited to the specific solvent, and any solvents can be used as long as they do not change the structure of the rare earth metal complexes. Examples other than THF include ether-based solvents (for example, diethyl ether and 1,4-dioxane), halogen-based solvents (for example, methylene chloride, chloroform, 1,1,1-trichloroethane and monochlorobenzene), hydrocarbon-based solvents (for example, benzene, toluene, n-hexane and n-heptane), and fatty acid esters (for example, ethyl acetate and methyl acetate), in addition, polar solvents such as dimethyl sulfoxide, N,N'-dimethylformamide, etc. can also be used. These solvents can be used in a single form or as a mixture of 2 or more types.

Examples of aldehydes used as a raw material for the process of the present invention include 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,5-trihydroxybenzaldehyde, 2,4,6-trihydroxybenzaldehyde, 2-hydroxy-3-hydroxymethylbenzaldehyde, 2-hydroxy-4-hydroxymethylbenzaldehyde, 2-hydroxy-5-hydroxymethylbenzaldehyde, 2-hydroxy-6-hydroxymethylbenzaldehyde, 3-hydroxy-2-hydroxymethylbenzaldehyde, 3-hydroxy-4-hydroxymethylbenzaldehyde, 3-hydroxy-5-hydroxymethylbenzaldehyde, 3-hydroxy-6-hydroxymethylbenzaldehyde, 4-hydroxy-2-hydroxymethylbenzaldehyde, 4-hydroxy-3-hydroxymethylbenzaldehyde, 4-hydroxy-5-hydroxymethylbenzaldehyde, 4-hydroxy-6-hydroxymethylbenzaldehyde, and the compounds as above of which aromatic hydroxyl group is protected with a hydroxyl-protective group (for example, t-butyldimethylsilyl group).

Examples of hydroxyl-protective groups used in the present invention include a methyl group, a tetrahydropyranyl group, an allyl group, an isopropyl group, a t-butyl group, a benzyl group, an acetyl group, and a trimethylsilyl group which are described in Protective Groups in Organic Synthesis.

Now the process for producing the optically active amino alcohol derivatives of the present invention will be described.

The optically active 1-substituted phenyl-2-amino alcohol derivatives of the present invention are synthesized by dissolving the corresponding optically active 1-substituted phenyl-2-nitroethanol compounds in an organic solvent, dispersing a catalytic hydrogen addition catalyst, and subjecting the optically active 1-substituted phenyl-2-nitroethanol compounds to hydrogen addition under hydrogen pressure.

Examples of the organic solvents include alcohols such as methanol, ethanol, n-propanol, isopropanol, n-butanol, isobutanol, and esters such as methyl acetate, ethyl acetate, propyl acetate, butyl acetate, methyl butyrate, and ethyl butyrate; however, the present invention is not intended to be limited to the specific solvent, and these alcohols and esters can be used in a single form or as a mixture in desired proportions.

For the catalytic hydrogen addition catalysts, usual hydrogen addition catalysts are satisfactory, and the examples include Pt—C, Pd—C and $PtO_2$.

Although the present invention is not intended to be limited to the specific amount of catalyst, considering the reaction time, 0.01 wt % or more of catalyst is preferably added based on the substrate (nitro alcohol).

Further, although the present invention is not intended to be limited to the specific reaction temperature, considering the intramolecular dehydration of nitro alcohols and the racemization of the products, the temperature is preferably 50° C. and below.

Further, although the present invention is not intended to be limited to the specific hydrogen pressure and preferably the pressure is in the range from 0.1 to 30 MPa, considering the production equipment, more preferably in the range from 0.1 to 1 MPa.

BEST MODE FOR CARRYING OUT THE INVENTION

The present invention is illustrated by the following embodiments and catalyst preparation examples, however, it is to be understood that the invention is not intended to be limited to the specific embodiments.

In each example, optical purity was determined by liquid chromatography (HPLC) (CHIRALPAK AD or CHIRALCEL OD by Daicel Chemical Industries, Ltd.). And $^1$H-NMR was measured with JNM-EX-270 (270 MHz) by JEOL.

CATALYST PREPARATION EXAMPLE 1

Preparation of Rare Earth Metal Complex Solution A0

58.0 mg (0.103 mmol) of (S)-6,6'-bis(triethylsilylethynyl)-1,1'-dihydroxy-2,2'-binaphthalene was dried in a vacuum at 50° C. for 2 hours. (S)-6,6'-bis(trimethylsilylethynyl)-1,1'-dihydroxy-2,2'-binaphthalene was dissolved in 880 μl of THF under an argon stream, and 172 μl of a solution of 11.3 mg (0.0344 mmol) of triisopropoxy samarium Sm $(Oi-Pr)_3$ in 0.2mol/$dm^3$ THF was added dropwise at 0° C. After stirring at room temperature for 30 minutes, 60 μl of a hexane solution of 1.72 mol/$dm^3$ n-BuLi (0.103 mmol) was added dropwise at 0° C. Then, the solution was stirred at room temperature overnight and 35 μl of THF solution containing water (0.035 mmol) was added, so as to prepare 0.03 mol/$dm^3$ THF solution of a complex catalyst (A0), as above.

CATALYST PREPARATION EXAMPLE 2

Preparation of Rare Earth Metal Complex Solution A1

54 µl of hexane solution of 1.72 mol/dm$^3$ n-BuLi (0.103 mmol) was added dropwise to the rare earth metal complex solution A0, so as to prepare a rare earth metal complex solution A1.

CATALYST PREPARATION EXAMPLE 3

Preparation of Rare Earth Metal Complex Solution B0

A rare earth metal complex solution B0 was prepared following the same procedure as in the preparation of the rare earth metal complex solution A0, except that lanthanum triisopropoxy La (Oi-Pr)$_3$ was used instead of samarium triisopropoxy Sm (Oi-Pr)$_3$.

CATALYST PREPARATION EXAMPLE 4

Preparation of Rare Earth Metal Complex Solution B1

54 µl of hexane solution of 1.72 mol/dm$^3$ n-BuLi (0.093 mmol) was added dropwise to the rare earth metal complex solution B0, so as to prepare a rare earth metal complex solution B1.

CATALYST PREPARATION EXAMPLE 5

Preparation of Rare Earth Metal Complex Solution C0

A rare earth metal complex solution C0 was prepared following the same procedure as in the preparation of the rare earth metal complex solution A0, except that dysprosium triisopropoxy Dy (Oi-Pr)$_3$ was used instead of Sm (Oi-Pr)$_3$.

CATALYST PREPARATION EXAMPLE 6

Preparation of Rare Earth Metal Complex Solution C1

54 µl of hexane solution of 1.72 mol/dm$^3$ n-BuLi (0.093 mmol) was added dropwise to the rare earth metal complex solution C0, so as to prepare a rare earth metal complex solution C1.

CATALYST PREPARATION EXAMPLE 7

Preparation of Rare Earth Metal Complex Solution D0

A rare earth metal complex solution D0 was prepared following the same procedure as in the preparation of the rare earth metal complex solution A0, except that gadolinium triisopropoxy Gd, (Oi-Pr)$_3$ was used instead of Sm (Oi-Pr)$_3$.

CATALYST PREPARATION EXAMPLE 8

Preparation of Rare Earth Metal Complex Solution D1

54 µl of hexane solution of 1.72 mol/dm$^3$ n-BuLi (0.093 mmol) was added dropwise to the rare earth metal complex solution D0, so as to prepare a rare earth metal complex solution D1.

CATALYST PREPARATION EXAMPLE 9

Preparation of Rare Earth Metal Complex Solution E0

A rare earth metal complex solution E0 was prepared following the same procedure as in the preparation of the rare earth metal complex solution A0, except that praseodymium triisopropoxy Pr (Oi-Pr)$_3$ was used instead of Sm (Oi-Pr)$_3$.

CATALYST PREPARATION EXAMPLE 10

Preparation of Rare Earth Metal Complex Solution E1

54 µl of hexane solution of 1.72 mol/dm$^3$ n-BuLi (0.093 mmol) was added dropwise to the rare earth metal complex solution E0, so as to prepare a rare earth metal complex solution E1.

CATALYST PREPARATION EXAMPLE 11

Preparation of Rare Earth Metal Complex Solution F1

A metal complex solution was prepared following the same procedure as in the preparation of the rare earth metal complex solution A0, except that (R)-1,1'-dihydroxy-2,2'-binaphthalene was used instead of (S)-6,6'-bis(triethylsilylethynyl)-1,1'-dihydroxy-2,2'-binaphthalene, after which 54 µl of hexane solution of 1.72 mol/dm$^3$ n-BuLi (0.093 mmol) was added dropwise, so as to prepare a rare earth metal complex solution F1.

EXAMPLE 1

Synthesis of (R)-1-(3,4-di(t-Butyldimethylsiloxy)phenyl)-2-nitroethanol 100 mg (0.26 mmol) of 3,4-di(t-butyldimethylsiloxy)benzaldehyde was dissolved in 10 ml of THF under the atmosphere of argon at −40° C., and 0.30 ml of rare earth metal complex solution A1 was mixed into the solution. After stirring for 30 minutes, 79.3 mg (1.3 mmol) of nitromethane was added dropwise to the mixture. After 67-hour reaction time, 2 ml of 1 N aqueous solution of hydrochloric acid was added to stop the reaction. Then, after 50 ml of ethyl accetate was added, the mixture was subjected to oil-water separation twice with 20 ml of saturated salt solution and once with 20 ml of water, and the ethyl accetate layer was dehydrated with sodium sulfate anhydride and concentrated within evaporator, followed by the purification of the concentrate by silica gel chromatography (n-hexane/acetone=10/1), after which (R)-1-(3,4-di(t-butyldimethylsiloxy)phenyl)-2-nitroethanol with an optical purity of 92% e.e. was obtained in a yield of 93%.

$^1$H-NMR (CDCl$_3$): δ 6.87–6.81 (m, 3H), 5.37–5.29 (m, 1H), 4.62–4.42 (m, 2H), 2.62 (br, 1H), 0.99 (s, 9H), 0.98 (s, 9H), 0.20 (s, 6H).

EXAMPLE 2

Synthesis of (R)-1-(3,4-di(t-Butyldimethylsiloxy)phenyl)-2-nitroethanol 110 mg (0.2.9 mmol) of 3,4-di(t-butyldimethylsiloxy)benzaldehyde was dissolved in 10 ml of THF under the atmosphere of argon at −40° C., and 0.32 ml of rare earth metal complex solution A0 was mixed into the solution.

After stirring for 30 minutes, 88.5 mg (1.45 mmol) of nitromethane was added dropwise to the mixture. After 67-hour reaction: time, (R)-1-(3,4-di(t-butyldimethylsiloxy) phenyl)-2-nitroethanol with an optical purity of 92% e.e. was obtained in a yield of 74%.

EXAMPLE 3

Synthesis of (R)-1-(3,4-Dimethoxyphenyl)-2-nitroethanol 100 mg (0.55 mmol) of 3,4-dimethoxybenzaldehyde was dissolved in 10 ml of THF under the atmosphere of argon at −40° C., and 0.60 ml of rare earth metal complex solution A1 was mixed into the solution. After stirring for 30 minutes, 168 mg (2.75 mmol) of nitromethane was added dropwise to the mixture. After 97-hour reaction time, (R)-1-(3,4-dimethoxyphenyl)-2-nitroethanol with an optical purity of 32% e.e. was obtained in a yield of 61%.

$^1$H-NMR (CDCl$_3$): δ 6.94–6.85 (m, 3H), 5.47–5.38 (m, 1H), 4.66–4.46 (m, 2H), 3.90 (s, 3H), 3.89 (s, 3H), 2.73 (br, 1H)

EXAMPLE 4

Synthesis of (R)-1-(3,4-Dibenzyloxyphenyl)-2-nitroethanol 100 mg (0.30 mmol) of 3,4-dibenzyloxybenzaldehyde was dissolved in 10 ml of THF under the atmosphere of argon at −40° C., and 0.33 m' of rare earth metal complex solution A1 was mixed into the solution. After stirring for 30 minutes, 91.6 mg (1.50 mmol) of nitromethane was added dropwise to the mixture. After 75-hour reaction time, (R)-1-(3,4-dibenzyloxyphenyl)-2-nitroethanol with an optical purity 59% e.e. was obtained in a yield of 90%.

$^1$H-NMR (CDCl$_3$): δ 7.45–7.20 (m, 10H), 7.00–6.86 (m, 3H), 5.38–5.26 (m, 1H), 5.17 (s, 2H), 5.16 (s, 2H), 4.57–4.38 (m, 2H), 2.67 (br, 1H)

EXAMPLE 5

Synthesis of (R)-1-(3,4-Diacetoxyphenyl)-2-nitroethanol 102 mg (0.43 mmol) of 3,4-diacetoxybenzaldehyde was dissolved in 10 ml of THF under the atmosphere of argon at −40° C., and 0.48 ml of rare earth metal complex solution A1 was mixed into the solution. After stirring for 30 minutes, 131 mg (2.15 mmol) of nitromethane was added dropwise to the mixture. After 68-hour reaction time, (R)-1-(3,4-diacetoxyphenyl)-2-nitroethanol with an optical purity of 59% e.e. was obtained in a yield of 87%.

$^1$H-NMR (CDCl$_3$): δ 7.32–7.19 (m, 3H), 5.55–5.40 (m, 1H), 4.63–4.42 (m, 2H), 2.62 (br, 1H), 2.30 (s, 3H), 2.29 (s, 3H)

EXAMPLE 6

Synthesis of (R)-1-(3,4-di(t-Butyldimethylsiloxy)phenyl)-2-nitroethanol 105 mg (0.28 mmol) of 3,4-di(t-butyldimethylsiloxy) benzaldehyde was dissolved in 10 ml of THF under the atmosphere of argon at −40° C., and 0.31 ml of rare earth metal complex solution D1 was mixed into the solution. After stirring for 30 minutes, 85.5 mg (1.40mmol) of nitromethane was added dropwise to the mixture. After 61-hour reaction time, (R)-1-(3,4-di(t-butyldimethylsilxy) phenyl)-2-nitroethanol with an optical purity of 87% e.e. was obtained in a yield of 86%.

EXAMPLE 7

Synthesis of (R)-1-(3,4-di(t-Butyldimethylsiloxy)phenyl)-2-nitroethanol 100 mg (0.26 mmol) of 3,4-di(t-butyldimethylsiloxy) benzaldehyde was dissolved in 10 ml of THF under the atmosphere of argon at −40° C., and 0.31 ml of rare earth metallcomplex solution B1 was mixed into the solution. After stirring for 30 minutes, 79.3 mg (1.30 mmol) of nitromethane was added dropwise to the mixture. After 66-hour reaction time, (R)-1-(3,4-di(t-butyldimethylsiloxy) phenyl)-2-nitroethanol with an optical purity of 79% e.e. was obtained in a yield of 89%.

EXAMPLE 8

Synthesis of (R)-1-(3,4-di(t-Butyldimethylsiloxy)phenyl)-2-nitroethanol 100 mg (0.26mmol) of 3,4-di(t-butyldimethylsiloxy) benzaldehyde was dissolved in 10 ml of THF under the atmosphere of argon at −40° C., and 0.31 ml of rare earth metal complex solution E1 was mixed into the solution. After stirring for 30 minutes, 79.3mg (1.30mmol) of nitromethane was added dropwise to the mixture. After 66-hour reaction time, (R)-1-(3,4-di(t-butyldimethylsiloxy) phenyl)-2-nitroethanol with an optical purity of 84% e.e. was obtained in a yield of 86%.

EXAMPLE 9

Synthesis of (R)-1-(3,4-di(t-Butyldimethylsiloxy)phenyl)-2-nitroethanol 102 mg (0.27 mmol) of 3,4-di(t-butyldimethylsiloxy) benzaldehyde was dissolved in 10 ml of THF under the atmosphere of argon at −40° C., and 0.30 ml of rare earth metal complex solution C1 was mixed into the solution. After stirring for 30 minutes, 82.4 mg (1.35 mmol) of nitromethane was added dropwise to the mixture. After 66-hour reactionitime, (R)-1-(3,4-di(t-butyldimethylsiloxy) phenyl)-2-nitroethanol with an optical purity of 68% e.e. was obtained in a yield of 72%.

EXAMPLE 10

Synthesis of (S)-1-(3,4-di(t-Butyldimethylsiloxy)phenyl)-2-nitroethanol

The rare earth metal complex solution F1 (10 ml) and 0.80 g (13.0 mmol) of nitromethane were mixed and stirred together for 30 minutes under the atmosphere of nitrogen. A solution of 1.00 g (2.6 mmol) of 3,4-di(t-butyldimethylsiloxy)benzaldehyde dissolved in 20 ml of THF was added dropwise to the mixture. After 24-hour reaction time, (S)-1-(3,4-di(t-butyldimethylsiloxy)phenyl)-2-nitroethanol with,an optical purity of 93% e.e. was obtained in a yield of 85%.

EXAMPLE 11

Synthesis of (R)-α-Nitromethyl-piperonyl alcohol (R)-α-nitromethyl-piperonyl alcohol with an optical purity of 73% e.e. was obtained from piperonal using the rare earth metal complex solution A1 under the atmosphere of argon at −40° C. after 50-hour reaction time.

$^1$H-NMR (CDCl$_3$): δ 6.90–6.82 (m, 3H), 5.99 (s, 2H), 5.41–5.35 (m, 1H), 4.62–4.43 (m, 2H), 2.70 (br, 1H)

EXAMPLE 12

Synthesis of Optically Active 1-(3,5-di(t-Butyldimethylsiloxy)phenyl)-2-nitroethanol 100 mg (0.26 mmol) of 3,5-di(t-butyldimethylsiloxy) benzaldehyde was dissolved in 10 ml of THF under the atmosphere of argon at −40° C., and 0.30 ml of rare earth metal complex solution A1 was mixed into the solution. After stirring for 30 minutes, 159 mg (2.6 mmol) of nitromethane was added dropwise to the mixture. After 140-hour reaction time, optically active 1-(3,5-di(t-butyldimethylsiloxy)phenyl)-2-nitroethanol with an optical purity of 62% e.e. was obtained in a yield of 93%.

$^1$H-NMR (CDCl$_3$): δ 6.86–6.83 (m, 3H), 5.34 (m, 1H), 4.57 (dd, J=13.3, 9.4 Hz, 1H), 4.46 (dd, J=13.3, 3.1 Hz, 1H), 2.64 (d, J=3.5 Hz, 1H), 0.9:9 (s, 9H), 0.98 (s, 9H), 0.20 (s, 12H)

EXAMPLE 13

Synthesis of Optically Active 1-(3,5-Dibenzyloxyphenyl)-2-nitroethanol 100 mg (0.30 mmol) of 3,5-dibenzyloxydibenzaldehyde was dissolved in 10 ml of THF under the atmosphere of argon at −40° C., and 0.35 ml of rare earth metal complex solution A1 was mixed into the solution. After stirring for 30 minutes, 183 mg (3.0 mmol) of nitromethane was added dropwise to the mixture. After 71-hour reaction time, optically active 1-(3,5-dibenzyloxyphenyl)-2-nitroethanol with an optical purity of 68% e.e. was obtained in a yield of 84%.

$^1$H-NMR (CDCl$_3$): δ 7.45–7.30 (m, 10H), 6.65–6.58 (m, 3H), 5.42–5.36 (m, 1H), 5.04 (s, 4H), 4.62–4.45 (m, 2H), 2.74 (d, 1H)

EXAMPLE 14

Synthesis of Optically Active 1-(3,5-Dibenzyloxyphenyl)-2-nitroethanol 100 mg (0.3 mmol) of 3,5-dibenzyloxydibenzaldehyde was dissolved in 10 ml of THF under the atmosphere of argon at −40° C., and 0.32 ml of rare earth metal complex solution A1 was mixed into the solution. After stirring for 30 minutes, 183 mg (29.9 mmol) of nitromethane was added dropwise to the mixture. After 88-hour reaction time, optically active 1-(3,5-dibenzyloxyphenyl)-2-nitroethanol with an optical purity of 88% e.e. was obtained in a yield of 100%. $^1$-H-NMR (CDCl$_3$): δ 7.45–7.30 (m, 10H), 6.65–6.58 (m, 3H), 5.42–5.36 (m, 1H), 5.04 (s, 4H), 4.62–4.45 (m, 2H), 2.74 (d, 1H)

EXAMPLE 15

Synthesis of Optically Active 1-(3,5-Diacetoxyphenyl)-2-nitroethanol 102 mg (0.43 mmol) of 3,5-diacetoxybenzaldehyde was dissolved in 10 ml, of THF under the atmosphere of argon at −40° C., and 0.45 ml of rare earth metal complex solution A1 was mixed into the solution. After stirring for 30 minutes, 262 mg (4.3 mmol) of nitromethane was added dropwise to the mixture. After 44-hour reaction time, optically active 1-(3,5-diacetoxyphenyl)-2-nitroethanol with an optical purity of 86% e.e. was obtained in a yield of 89%.

$^1$H-NMR (CDCl$_3$): δ 7.07 (d, 2H), 6.91 (t, 1H), 5.48–5.41 (m, 1H), 4.61–4.48 (m, 2H), 3.03 (d, 1H), 2.29 (s, 6H)

EXAMPLE 16

Synthesis of Optically Active 1-(4-t-Butyldimethylsiloxy-3-t-butyldimethylsiloxymethylphenyl)-2-nitroethanol The rare earth metal complex solution A1 (0.10 ml) and 66 mg (1.07 mmol) of nitromethane were stirred at −40° C. for 30 minutes, then 0.39 ml of solution of 41 mg (0.11 mmol) of 4-t-butyldimethylsiloxy-3-t-butyldimethylsiloxymethylbenzaldehyde in THF was added dropwise to the mixture. After 69-hour reaction time, optically active 1-(4-t-butyldimethylsiloxy-3-t-butyldimethylsiloxymethylphenyl)-2-nitroethanol with an optical purity of 37% e.e. was obtained in a yield of 35%.

$^1$H-NMR (CDCl$_3$): δ 7.47 (d, j=2.0 Hz, 1H) , 7.16 (dd, j=8.5, 2.0 Hz, 1H), 6.76 (d, j=8.5 Hz, 1H), 5.41 (dd, j=9.5, 3.5, 3.0 Hz, 1H), 4.74 (s, :2H), 4.61 (dd, j=13.5, 9.0 Hz, 1H), 4.48 (dd, j=13.5, 3.0 Hz, 1H), 2.65 (d, j=3.5 Hz, 1H), 1.00 (s, 9H), 0.96 (s, 9H), 0.22 (s, 6H), 0.11 (s, 6H)

EXAMPLE 17

Synthesis of Optically Active 2,2-Dimethyl-α-nitromethyl-1,3-benzodioxane-6-methanol 100 mg (0.52 mmol) of 2,2-dimethyl-1,3-benzodioxane-6-acetoaldehyde was dissolved in 1.9 ml of THF under the atmosphere of argon at −40° C., and the rare earth metal complex solution A1 was mixed into the solution. After stirring for 30 minutes, 318 mg (5.2 mmol) of nitromethane was added dropwise to the mixture. After 61-hour reaction time, optically active 2,2-dimethyl-α-nitromethyl-1,3-benzodioxane-6-methanol with an optical purity of 87% e.e. was obtained in a yield of 86%.

EXAMPLE 18

Synthesis of Optically Active 1-(4-t-Butyldimethylsiloxy-3-t-butyldimethylsiloxymethylphenyl)-2-nitroethanol The rare earth metal complex solution B1 and 65 mg (1.07 mmol) of nitromethane were stirred at −40° C. for 30 minutes, then 0.40 ml of solution of 42 g (0.11 mmol) of 4-t-butyldimethylsiloqxy-3-t-butyldimethylsiloxymethylbenzaldehyde in THF was added dropwise to the mixture. After 67-hour reaction time, optically active 1-(4-t-butyldimethylsiloxy-3-t-butyldimethylsiloxymethylphenyl)-2-nitroethanol with an optical purity of 30% e.e. was obtained in a yield of 30%.

EXAMPLE 19

Synthesis of Optically Active 1-(4-Benzoyloxy-3-benzoyloxymethylphenyl)-2-nitroethanol The rare earth metal complex solution A1 and 149 mg (2.44 mmol) of nitromethane were stirred at −40° C. for 30 minutes, then 0.89 ml of solution of 88 mg (0.24 mmol) of 4-benzoyloxy-3-benzoyloxymethylbenzaldehyde in THF was added dropwise to the mixture. After 69-hour reaction time, optically active 1-(4-benzoyloxy-3-benzoyloxymethylphenyl)-2-nitroethanol with an optical purity of 64% e.e. was obtained in a yield of 86%.

EXAMPLE 20

Synthesis of Optically Active 1-(4-Benzoyloxyphenyl)-2-nitroethanol

Optically active 1-(4-benzoyloxyphenyl)-2-nitroethanol with an optical purity of 50% e.e. was obtained from

EXAMPLE 21

Synthesis of Optically Active 1-(4-Benzoyloxyphenyl)-2-nitropropanol (S,S)-1-(4-benzoyloxyphenyl)-2-nitropropanol (30% e.e.), the threo form/erythro form ratio is 1.8/1.0, was obtained from 4-benzoyloxybenzaldehyde and nitroethane using the rare earth metal complex solution F1 under the atmosphere of nitrogen at −30° C. after 24-hour reaction time.

EXAMPLE 22

Synthesis of (R)-(−)-1-(3,4-di(t-Butyldimethylsiloxy)phenyl)-2-aminoethanol 100 mg of optically active 1-(3,4-di(t-butyldimethylsiloxy)phenyl)-2-nitroethanol obtained in example 1 was dissolved in 10 ml of methanol, and 10 mg of 10% Pd/C was added to the solution, after which the mixture was reacted at 20° C. under the hydrogen pressure of 0.1 MPa for 20 hours, so as to obtain 89.3 mg of the intended compound (in a yield of 96%, with an optical purity of 94% e.e.). IR (neat) cm$^{-1}$: 3859, 2928

$^1$H-NMR (CDCl$_3$): δ 6.85–6.76 (m, 3H), 4.54 (dd, j=8.0, 4.0 Hz, 1H), 2.97 (dd, j=12.0, 4.0 Hz, 1H), 2.81 (dd, j=12.0, 8.0 Hz, 1H), 0.98 (5, 18H), 0.19 (s, 12H) $^{13}$C-NMR (CDCl$_3$, 97.9 MHz): 146.7, 146.3, 135.5, 120.8, 118.8, 73.7, 49.1, 25.9, 18.4, −4.1

$[\alpha]^{25}_D$=−21.9 (c1.15, CHCl$_3$).

EXAMPLE 23

Synthesis of (S)1-1-(3,4-di(t-Butyldimethylsiloxy)phenyl)-2-aminoethanol 98 mg of (S)-1-(3,4-di (t-butyldimethylsiloxy)phenyl)-2-nitroethanol obtained in example 10 was dissolved in 10 ml of methanol, and 10 mg of 10% Pd/C was added to the solution, after which the mixture was reacted at 20° C. under the hydrogen pressure of 0.3 MPa for 5 hours, so as to obtain 85 mg of the intended compound.

$[\alpha]^{25}_D$=+21.5 (c1.10, CHCl$_3$).

EXAMPLE 24

Synthesis of Optically Active 1-(3,5-Dibenzoyloxyphenyl)-2-aminoethanol

The intended compound with an optical purity of 12% e.e. was obtained in alyield of 12% from the optically active 1-(3,5-dibenzoyloxyphenyl)-2-nitroethanol obtained in example 14 using 10% Pd/C.

$[\alpha]^{25}_D$=−2.3 (c0.32, EtOH)

EXAMPLE 25

Synthesis of Optically Active 1-(4-t-Butyldimethylsiloxy-3-t-butyldimethylsiloxymethylphenyl)-2-aminoethanol The intended compound was obtained from the optically active 1-(4-t-butyldimethylsiloxy-3-t-butyldimethylsiloxymethylphenyl)-2-nitroethanol obtained in example 18 using 10% Pd/C.

$[\alpha]^{25}_D$=−2.9 (c0.35, EtOH)

EXAMPLE 26

Synthesis of Optically Active α-Aminomethyl-2,2-dimethyl-1,3-benzodioxane-6-methanol The intended, compound was obtained from the optically active 2,2-dimethyl-α-nitromethyl-1,3-benzodioxane-6-methanol obtained in example 17 using 10% Pd/C.

$[\alpha]^{25}_D$=−2.2 (c0.25, EtOH)

EXAMPLE 27

Synthesis of (R)-Albutamin 89.3 mg of (−)-1-(3,4-di(t-butyldimethylsiloxy)phenyl)-2-aminoethanol, 50.0 mg of 4-(4-methoxymethoxyphenyl)butanoic acid, diethylphosphorylcyanide, and triethylamine were dissolved in N,N-dimethylformamide at 0° C., reacted at room temperature, so as to obtain 108.6 mg (in a yield of 82%) of amide compound. The amide compound obtained was reduced with lithium aluminium halide in an ether solvent at reflux temperature, so as to quantitatively obtain amine. And 55.6 mg of (R)-albutamin which is the intended compound was obtained by deprotecting the hydroxyl-protective group of the amine in a methanol—THF solvent at room temperature using hydrochloric acid.

$[\alpha]^{25}_D$=−17 (c1.15, EtOH)

EXAMPLE 28

Synthesis of (R)-Sarmeterol

Amine was obtained from the optically active 2,2-dimethyl-α-aminomethyl-1,3-benzodioxane-6-methanol synthesized in example 26 and 6-(1-phenyl-butoxy) hexaaldehyde through subjecting them to reduction and amination, then the hydroxyl-protective group of the amine compound was deprotected using hydrochloric acid, so as to obtain the intended compound, (R)-sarmeterol. The angle of rotation was measured using the compound's salt of hydroxy naphthoic acid.

$[\alpha]^{24}_D$=−3.1 (c0.30, MeOH)

Industrial Availability

As described above, according to the present invention, optically active 1-substituted phenyl-2-nitro alcohol derivatives and optically active 1-substituted phenyl-2-amino alcohol derivatives, which are useful as pharmaceutical intermediates, and, in addition, the process for producing these compounds can be provided using a specific group of rare earth metal complexes.

Specifically, according to the present invention, optically active 1-substituted phenyl-2-nitro alcohol derivatives which are used as a material for pharmaceuticals, such as (R)-albutamin, have been synthesized, and the process for producing thereof has been established.

At the same time, the process for producing optically active 1-substituted phenyl-2-amino alcohol derivatives which are to become useful intermediates of pharmaceuticals from optically active 1-substituted phenyl-2-nitro alco hol derivatives has been established, and the process for producing pharmaceuticals, (R)-albutamin and (R)-sarmeterol, from optically active 1-substituted phenyl-2-amino ethanol derivatives has been established.

What is claimed is:

1. An optically active alcohol of the following formula (1-1)

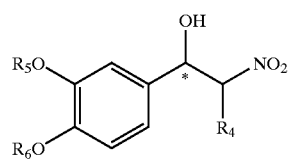

(Formula 1-1)

in which $R_5$ and $R_6$ both represent a t-butyldimethylsilyl group, respectively; $R_4$ represents a hydrogen atom; and * represents an optically active site.

* * * * *